United States Patent
Chen et al.

(10) Patent No.: US 11,302,444 B2
(45) Date of Patent: Apr. 12, 2022

(54) SYSTEM AND METHOD FOR COMPUTER AIDED DIAGNOSIS OF MAMMOGRAMS USING MULTI-VIEW AND MULTI-SCALE INFORMATION FUSION

(71) Applicant: Boston Meditech Group Inc., Burlington, MA (US)

(72) Inventors: Daniel Q. Chen, Concord, MA (US); Aditya Shirvalkar, Somerville, MA (US); Thomas Boot, Cambridge, MA (US); Yang Yu, San Jose, CA (US); Humayun Irshad, Union City, CA (US)

(73) Assignee: BOSTON MEDITECH GROUP INC., Burlington, MA (US)

( * ) Notice: Subject to any disclaimer, the term of this patent is extended or adjusted under 35 U.S.C. 154(b) by 58 days.

(21) Appl. No.: 16/888,643

(22) Filed: May 29, 2020

(65) Prior Publication Data

US 2021/0375458 A1    Dec. 2, 2021

(51) Int. Cl.
*G16H 50/20* (2018.01)
*G06T 7/44* (2017.01)
(Continued)

(52) U.S. Cl.
CPC ............. *G16H 50/20* (2018.01); *G06T 5/008* (2013.01); *G06T 5/009* (2013.01); *G06T 7/0012* (2013.01);
(Continued)

(58) Field of Classification Search
CPC . G06T 2207/30068; G06T 2207/10116; G06T 7/0012; G06T 2207/20081; G06T 2207/30096; G06T 2207/20084; G06T 5/50; G06T 7/11; G06T 3/4046; G06T 7/10; G06T 7/44; G06T 5/009; G06T 5/008;
(Continued)

(56) References Cited

U.S. PATENT DOCUMENTS 10,037,601 B1 *   7/2018  Ben-Ari ............... G06K 9/6226
2016/0314579 A1 * 10/2016  Ghouti ................. G06K 9/3241
(Continued)

OTHER PUBLICATIONS

Abdullah-Al Nahid and Yinan Kong Involvement of Machine Learning for Breast Cancer Image Classification: A Survey Computational and Mathematical Methods in Medicine vol. 2017, Article ID 3781951, 29 pages (Year: 2017).*
(Continued)

*Primary Examiner* — Nizar N Sivji
(74) *Attorney, Agent, or Firm* — Lorenz & Kopf, LLP (57) ABSTRACT

A system and method for processing mammographic images of target breast tissue is provided. The mammographic images are processed to generate modified images. A deep learning algorithm, having a tailored Convolutional Neural Networks (CNN) model, is applied to the modified images to generate a first output and a second output. Global features associated with the entirety of the mammographic images are extracted by using the first output. Local features associated with Regions of Interest (ROIs) of the mammographic images are extracted by using the second output. The global features and the local features are combined and fuse to generate an indicator representative of likelihood of malignancy of the target breast tissue.

15 Claims, 8 Drawing Sheets

(51) Int. Cl.
   *G06T 7/00* (2017.01)
   *G06T 5/00* (2006.01)
(52) U.S. Cl.
   CPC ...... *G06T 7/44* (2017.01); *G06T 2207/10116* (2013.01); *G06T 2207/20008* (2013.01); *G06T 2207/20012* (2013.01); *G06T 2207/20032* (2013.01); *G06T 2207/20084* (2013.01); *G06T 2207/20182* (2013.01); *G06T 2207/30068* (2013.01)
(58) Field of Classification Search
   CPC . G06T 2207/20032; G06T 2207/20012; G06T 2207/20008; G06T 2207/20182; G16H 50/20
   See application file for complete search history.

(56) References Cited

U.S. PATENT DOCUMENTS

2018/0075628 A1* 3/2018 Teare .................. G06K 9/6274
2019/0304092 A1* 10/2019 Akselrod-Ballin ....... G06T 7/13
2020/0372637 A1* 11/2020 Ha ........................... G06T 5/50

OTHER PUBLICATIONS

Dheeba J—Screening Mammogram Images for Abnormalities using Radial Basis Function Neural Network (Year: 2010).*
Cancer Diagnosis Using Deep Learning: A Bibliographic Review—2019 (Year: 2019).*
Breast Cancer Detection and Diagnosis Using MammographicData: Systematic Review—2019 (Year: 2019).*
Application of texture analysis method for mammogram density classification—2017 (Year: 2017).*
Dilated Semantic Segmentation for Breast Ultrasonic Lesion Detection Using Parallel Feature Fusion—2021 (Year: 2021).*
Fully Convolutional Networks for Semantic Segmentation—2015 (Year: 2015).*
A State-of-the-Art Survey on Deep Learning Methods for Detection of Architectural Distortion From Digital Mammography—2020 (Year: 2020).*

* cited by examiner

SYSTEM AND METHOD FOR COMPUTER AIDED DIAGNOSIS OF MAMMOGRAMS USING MULTI-VIEW AND MULTI-SCALE INFORMATION FUSION

FIELD

This disclosure generally relates to medical image processing. More specifically, this disclosure relates to a computer-aided diagnostic method and system for processing mammographic images to annotate, assess and predict likelihood or probability of suspected malignancy and abnormalities in breast tissue.

BACKGROUND

Digital mammograms are X-ray images generated in breast imaging. Reviewing and studying mammograms are typically the first step in assessing the health of the breast tissue and diagnosing any suspicious lumps that may have been found upon undergoing a physical examination. For any person who is subject to a mammography exam, four images in total are typically taken, two for each breast. For a given breast, typically two images are taken in two different views. In most cases, these two views are preferably a Craniocaudal (hereinafter "CC") view and a Mediolateral Oblique (hereinafter "MLO") view.

After a mammogram is generated, radiologists typically assign these images with a Bi-Rads score. The score extrapolates and indicates diagnostic information contained in the mammogram. Typically, a score less than 2 is considered to contain no signs of malignancy. A score higher than 2 indicates possible malignancies, and the scores 3, 4a, 4b, 4c, 5, and 6 all indicate malignancies but with varying levels of confidence. These scores are based on subjective assessment by a radiologist and thus, have very low repeatability. This can cause undergoing unnecessary procedures and unwanted mental stress to the patient. Computer Aided Detection (hereinafter "CAD") techniques can assist radiologists in providing second opinions that are based on quantitative assessment of mammograms, which have high repeatability with almost zero variance.

A breast, as known, is a 3-D structure. In an X-ray exam, the 3-D structure of the breast is mapped onto a 2-D plane. The mapping process can be considered summation of multiple images into one image. An underlying deficiency associated with this mapping technique is that certain parts of the resulting image may appear differently, which can give false positives (positives being associated with malignancy) and false negatives (negative being associated with benignity). For example, considering one view of a breast to be a summation of information from 100 images, at any given location in the image, the pixel values have a contribution from a depth of 100 images. Thus, if an abnormality exists in certain frames in the image at a particular location, the abnormality also has contributions from frames that were completely benign at that location. This can cause the abnormal region to appear differently, which can have a direct impact on the confidence of the decisions that the system makes.

Furthermore, most of the existing CAD systems use information obtained only from one view of the breast or only at one scale to make a decision. This approach can cause the algorithms to generate false detections or decisions with low confidence. In addition, the system architecture of the existing CAD systems is based on the detection-classification framework, in which individual abnormalities are detected in a first stage and the detected abnormalities are subsequently classified in a second stage.

The existing CAD systems have certain underlying deficiencies. First, these systems only operate on abnormalities present in the breast and completely neglect any naturally occurring pathologies that are highly correlated with occurrence of tumors. Secondly, the two stage approach is prone to false positives, as even if one of the detected abnormalities is wrongly classified as malignant, the entire image is given a malignant label.

Therefore, it is desirable to develop reliable and advanced technologies to processing mammographic images to annotate, assess and predict likelihood or probability of suspected malignancy and abnormalities in breast tissue.

SUMMARY OF DISCLOSURE

According to an aspect of the present disclosure, a computer aided diagnostic method for processing mammographic images of target breast tissue is provided. The method includes processing the mammographic images to generate at least one modified image. The method further includes applying a deep learning algorithm including a tailored Convolutional Neural Networks (CNN) model to the at least one modified image to generate a first output and a second output. The method further includes extracting global features associated with the entirety of the mammographic images by using the first output. The method further includes extracting local features associated with Regions of Interest (ROIs) of the mammographic images by using the second output. The method further includes combining the global features and the local features to generate an indicator representative of likelihood of malignancy of the target breast tissue.

According to another aspect of the present disclosure, a system for processing mammographic images of target breast tissue is provided. The system includes a hardware processor and a memory coupled with the hardware processor. The hardware processor is configured to at least: process the mammographic images to generate at least one modified image; apply a deep learning algorithm including a tailored Convolutional Neural Networks (CNN) model to the at least one modified image to generate a first output and a second output; extract global features associated with the entirety of the mammographic images by using the first output; extract local features associated with Regions of Interest (ROIs) of the mammographic images by using the second output; and combine the global features and the local features to generate an indicator representative of likelihood of malignancy of the target breast tissue.

According to another aspect of the present disclosure, a computer program product for processing mammographic images of target breast tissue is provided. The computer program product includes a computer readable storage medium having program instructions embodied therewith. The program instructions are executable by a processing element of a device to cause the device to: process the mammographic images to generate at least one modified image; apply a deep learning algorithm including a tailored Convolutional Neural Networks (CNN) model to the at least one modified image to generate a first output and a second output; extract global features associated with the entirety of the mammographic images by using the first output; extract local features associated with Regions of Interest (ROIs) of the mammographic images by using the second output; and combine the global features and the local features to generate an indicator representative of likelihood of malignancy of the target breast tissue.

DETAILED DESCRIPTION

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following descriptions, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

In a broad sense, an aspect of the disclosure of the present application utilizes information from both CC and MLO views and at multiple scales to create algorithms, which are robust to false detections that are caused by most single-view CAD techniques. By using the algorithms, confidence of diagnosis by the system can be improved. As a result, the underlying deficiencies of the existing CAD systems can be reasonably overcome.

In addition, another aspect of the disclosure is directed to a deep learning based system and method, which requires fusion of information at multiple scales for multiple views of the breast to generate likelihood scores for the presence of malignancies in the breast. The deep learning based system and method is achieved by a multi-step process, which will be articulated in the following. By utilizing information extracted from multiple views and multiple scales, the deep learning based system and method is capable of decreasing of false positives and increasing the confidence with which a prediction is made.

Figure 1:
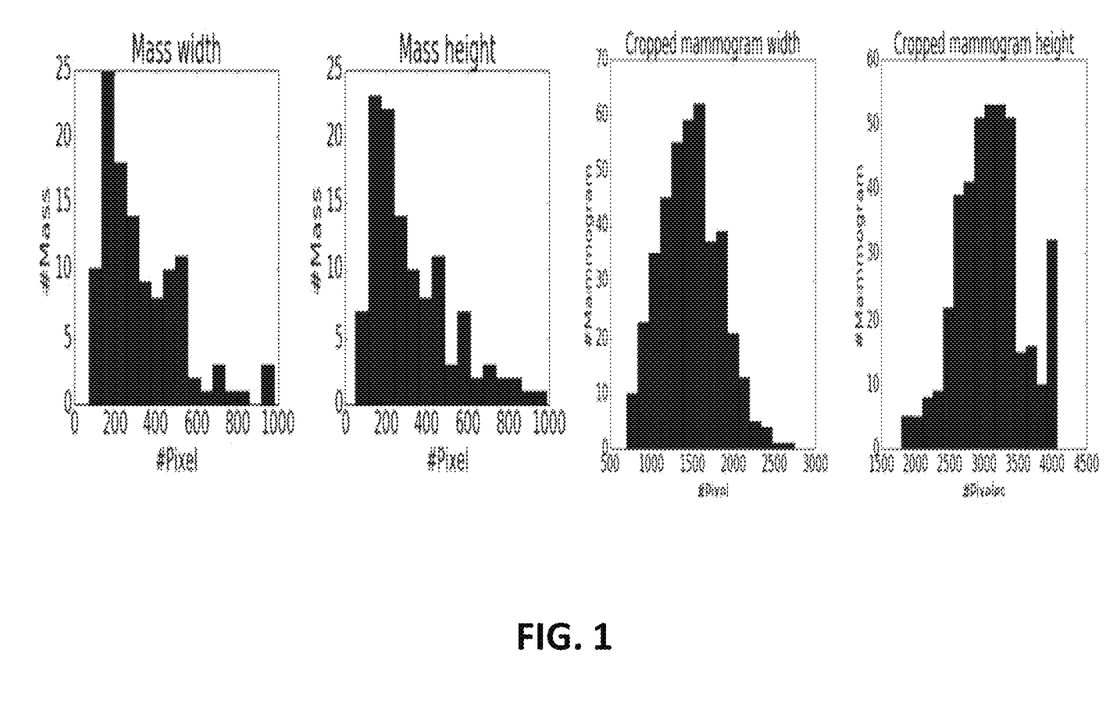
FIG. 1 is a diagram illustrating an analysis of mass dimensions of abnormalities present in a breast and the dimensions of the breast.

Abnormalities present in breasts are normally significantly small, when the abnormalities are being compared to the size of the entire image. Typically, the area occupied by a mass of abnormalities can be about 2-3% of the area of the entire breast mammogram image, and can be even lower for calcifications. FIG. 1 shows an analysis made on the size of the mass and calcification on the popular public dataset CBIS-DDSM. As evident from the analysis, the mass size varies in a range.

Since the ratio between the area of features of interest and the image is significantly low, solely using whole mammograms with traditional Convolutional Neural Networks (hereinafter "CNN") based systems can lead to poor results or results with low confidence. Even though CNNs have proven to be highly accurate in image classification tasks, the successive reduction in the size of the feature maps due to pooling operations can occasionally lead to information loss, when the features of interest are small. According to another aspect of the disclosure, to increase robustness of the method and system against the information loss, CNNs are utilized for feature extraction. For example, CNNs can be used to extract complex non-linear representations from an input image and to provide Regions of Interest (hereinafter "ROIs"), which are locations in the image with high probability of malignancy. From these representations, both local features and global features can be extracted. For example, the local features can be features extracted at a higher scale and from specific or predetermined regions, while the global features can be extracted at a lower scale and from the entire image.

The system and method of the disclosure requires a plurality of different steps for processing mammographic images.

For example, according to a first step, raw dicom images are processed to remove any noise or artifacts that may have been added due to image acquisition process or due to other reasons. In this step, the input image is first normalized to be in the range of 0 to 1 'float32' values. The normalized image is subsequently processed with median filtering and adaptive histogram equalization to enhance tissue to background contrast.

For example, according to a second step, a deep learning algorithm or model is applied. In this step, two different outputs are generated from two intermediate layers of the deep learning model. The first output is utilized for a so-called ROI detection. The second output is used as it is, and the features generated at this output are considered global features.

For example, according to a third step, the ROI detection stage is implemented. In this step, the output from the second step is utilized to create one or more probability heatmaps for the input image. These probability heatmaps indicate parts of the image, which highly contribute towards a particular diagnosis made by the CNN. For local feature extraction, the images of the probability heatmaps are subject to a threshold to select specific ROIs, and the these ROIs are subsequently utilized to compute morphology, intensity and texture features from the processed image (i.e., smoothed and enhanced image) and the probability heatmap images. These local and global features are generated for both CC and MLO images and combined to create an input.

For example, according to a fourth step, a classification algorithm is applied to generate a likelihood score for the input image. In this step, initially, certain feature selection techniques are applied to select certain features of significance from the input created in the third step (such as, an input feature vector), thereby removing redundant features for the purpose of saving computation time towards making the final decision. Subsequently, am algorithm (such as, a Random Forest classifier) is applied for further classification, which generates the final likelihood score.

Figure 2:
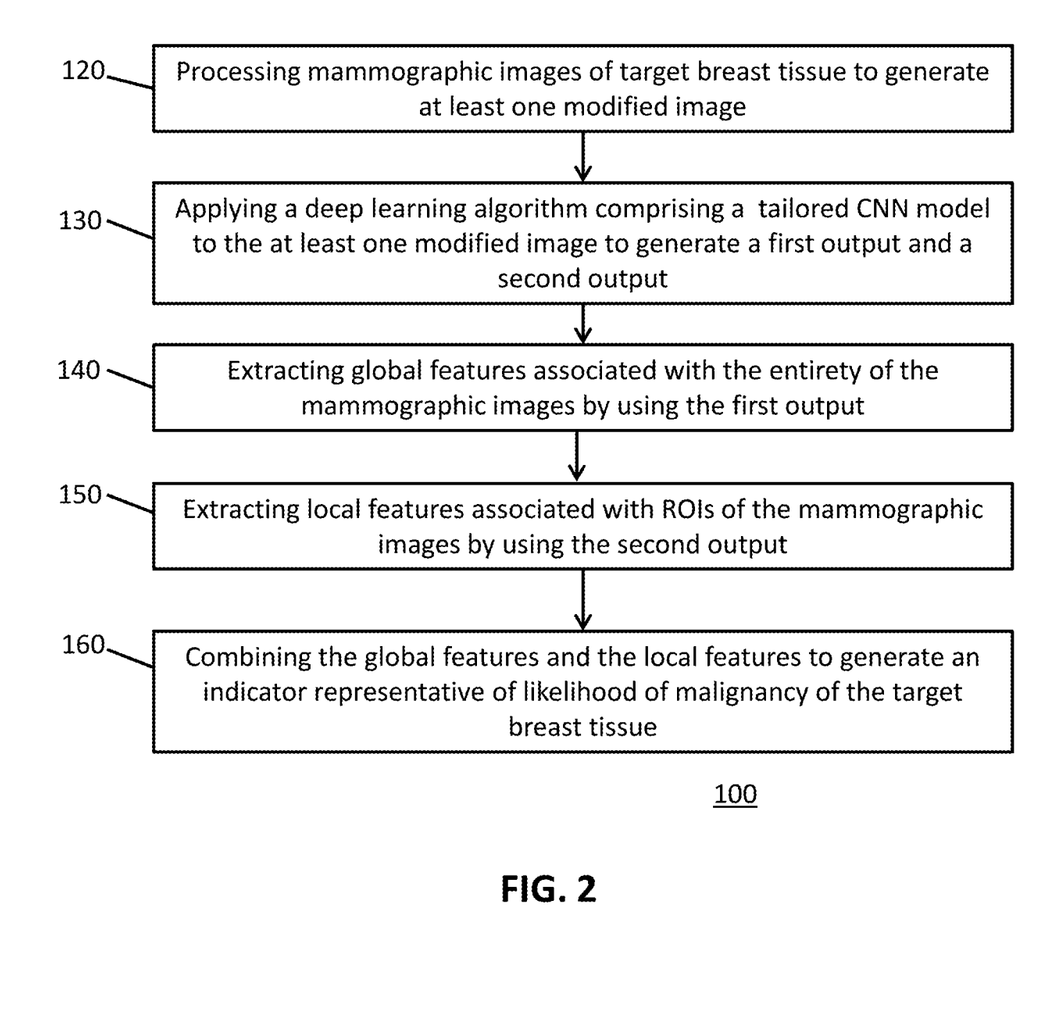
FIG. 2 is a flow diagram illustrating a computer-aided diagnostic process according to an embodiment of the disclosure.

FIG. 2 is a flow diagram illustrating a computer-aided diagnostic process 100 for processing mammographic images to annotate, assess and predict likelihood or probability of suspected malignancy and abnormalities in breast tissue. An example process may include one or more operations, actions, or functions as illustrated by one or more of blocks 120, 130, 140, 150 and/or 160. Although illustrated as discrete blocks, various blocks can be divided into additional blocks, combined into fewer blocks, eliminated, or performed in parallel, depending on the desired implementation.

The process 100 can start at the block 120. At the block 120, mammographic images of target breast tissue are processed to generate at least one modified image. At the block 130, a deep learning algorithm comprising a tailored CNN model is applied to the at least one modified image to generate a first output and a second output. At the block 140, global features associated with the entirety of the mammographic images are generated by using the first output. At the block 150, local features associated with certain ROIs of the mammographic images are generated by using the second output. At the block 160, the global features and the local features are combined to generate an indicator representative of likelihood of malignancy oftarget breast tissue. All these blocks can be implemented by one or more processor, such as, a hardware processor programmed with software.

Figure 3:
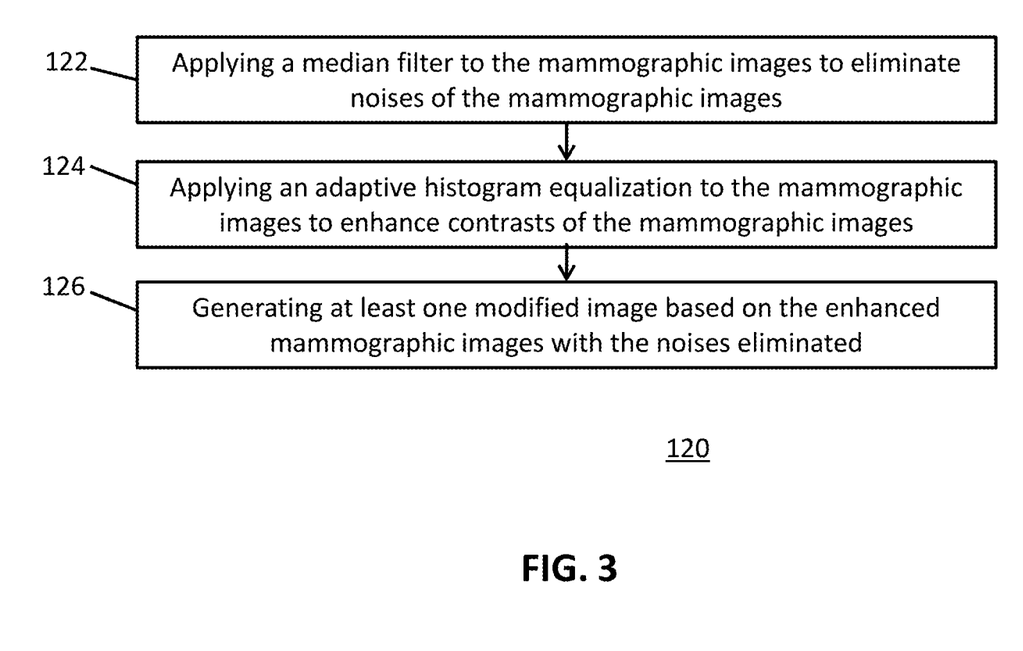
FIG. 3 is a flow diagram illustrating a process of FIG. 2.

At the block 120, the mammographic images are processed to generate one or more modified images. For example, the mammographic images of the target breast tissue can be processed to improve qualities and properties of the images and to remove certain undesirable features of the images. The mammographic images of the target breast tissue can be raw dicom images, which are obtained from an image acquisition device, such as, an X-ray device. The details of the block 120 are shown in FIG. 3.

At block 122, a median filter is applied to the mammographic images to eliminate any background noise and/or artifacts that may be introduced to the mammographic images during the process of obtaining and initial processing of these images. The median filer is a filtering algorithm, which is considered efficient to remove high frequency noise from images. The filtering algorithm can use an n*n mask, which is centered at every pixel in each image. The pixel is replaced with the median of the pixels in the neighborhood of the mask. For example, a 3*3 filter can be used. The size of this filter can be of any suitable value, although larger filter sizes can affect the image features leading to degradation in the image quality.

At block 124, adaptive histogram equalization is applied to the mammographic images to enhance contrasts of the mammographic images. As recognized, abnormalities present in the target breast tissue normally have a higher contrast in comparison with healthy breast tissue. Thus, implementation of contrast-enhancement of the mammographic images can allow the contrast difference more pronounced, which assists in making better and reliable predictions. The adaptive histogram equalization is effective due to presence of high variations in the image intensities due to different machines and exposure time. A major part of each mammographic image is normally made up of black background pixels, while the intensity within the target breast tissue shows high variability, with a higher mean intensity in dense breasts compared to that in fatty breasts. The adaptive histogram equalization can be applied selectively in local regions of each image, rather than the entire image. The size of the local regions can be selectively decided by users. For example, a **30*30** region can be decided.

At block 126, at least one modified image is generated, based on the enhanced mammographic images with the noises eliminated, and subsequently outputted.

At the block 130, a deep learning algorithm comprising a tailored CNN model is applied to the at least one modified image to generate a first output and a second output. For example, the tailored CNN model can generate intermediate representations as the first output and the second output, which are used for global features extraction and local features extraction, respectively.

The tailored CNN model can be a derivative or tailored modification of the known VGG16 model architecture, for classifying entire mammogram images. The tailored CNN model includes an algorithm, which applies a set of non-linear operations on the mammographic images to extract distinguishing features from these images for classification into respective classes. A core part of the algorithm includes stacks of convolutional filters, which every layer of the tailored CNN model uses. These filters extract important features from the mammographic images, which range from edges and curves in the lower layers of the tailored CNN to more structured set of features (such as, dense circular objects) in the higher layers of the tailored CNN.

Figure 4:
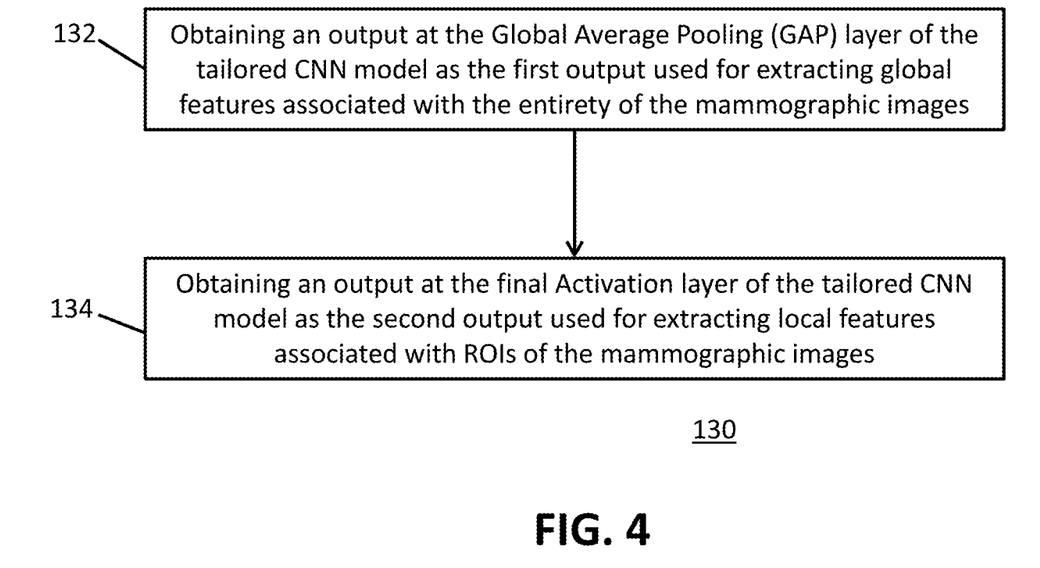
FIG. 4 is a flow diagram illustrating a process of FIG. 2.

The tailored CNN model can be initially trained to classify the entire mammogram images as benign or malignant. In addition, the intermediate representations generated by the tailored CNN model can be used to generate the first output and the second output. As shown in FIG. 4, at block 132, an output is obtained at the Global Average Pooling (hereinafter "GAP") layer of the tailored CNN model as the first output used for extracting global features associated with the entirety of the mammographic images. At block 134, an output is obtained at the final Activation layer of the tailored CNN model as the second output used for extracting local features associated with ROIs of the mammographic images that can be detected and identified.

At the block 140, global features associated with the entirety of the mammographic images are generated by using the first output.

The first output is an output generated by the GAP layer of the tailored CNN. The first output is a single dimensional vector of size 512. The features defined or acquired through this vector are considered the global features associated with the entirety of the mammographic images. For example, these features are generated by the tailored CNN after processing each image as whole and, thus contain information related to multiple locations of the mammogram. These features can assist the users to obtain information from areas in the target breast, which may show no direct signs of a malignancy but can be seen as contributors towards occurrence of malignancies in breast tissue. These global features can also assist the users to acquire key details from each mammogram image as a whole, which can include breast density and shape of the breast which are known to indicate an increased risk for breast health. These global features can also contain information on the presence of lymph nodes in the pectoral muscle. These lymph nodes can also present certain abnormalities, especially in the case of metastasis of a tumor in the body.

Figure 5:
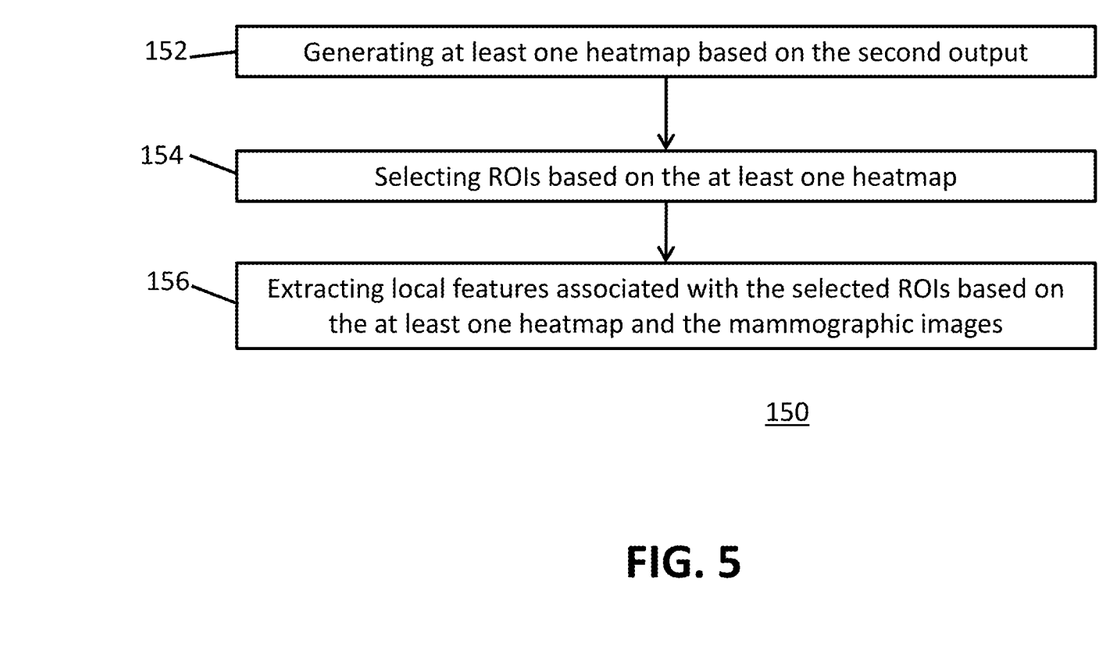
FIG. 5 is a flow diagram illustrating a process of FIG. 2.

At the block 150, local features associated with certain ROIs of the mammographic images are generated by using the second output. An output obtained at the final Activation layer of the tailored CNN model is used as the second output used for extracting local features associated with ROIs of the mammographic images that can be detected and identified. The details of the block 150 are shown in FIG. 5.

Figure 6:
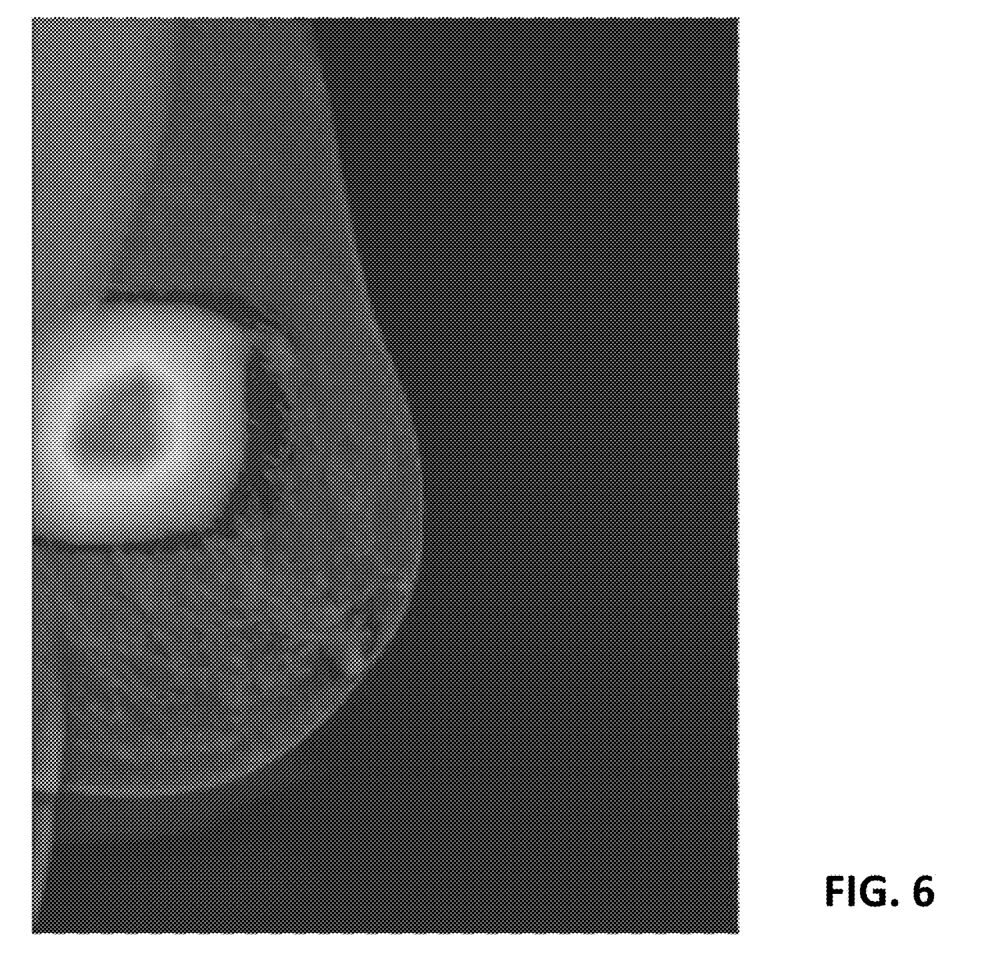
FIG. 6 is a diagram illustrating an example of a heatmap generated by tht process of FIG. 5.

At block 152, one or more heatmaps are generated based on the second output. These heatmaps are probability heatmaps generated based on the second output, taking into consideration of other factor including the trained weight at the final Activation layer of the tailored CNN model. These heatmaps indicate regions in the mammographic images, where there is high probability for the existence of any malignancy. Each generated heatmap is a map of the size same as the input image, with every pixel in the map having a value equal to the probability of the same pixel in the original image being malignant. An example of such a heatmap is shown in FIG. 6.

For example, the output at the final Activation layer is a 3D stack of features, of shape 18×14×512 and the weights obtained from the last layer of the CNN are of the size 1×512. These weights are used to get a weighted sum of the activation layer output, resulting in a single 18×14 heatmap. The heatmaps are calculated using the following equation.

$$Hmap = \sum_{i=0}^{512} y_{activation}(18 \times 14, i) \cdot w_{lastlayer}(i)$$

Where, $y_{activation}(18 \times 14, i)$ is the $i^{th}$ feature map at the output of the activation layer and $w_{lastlayer}(i)$ is the $i^{th}$ weight obtained from last layer weights. The resulting heatmap of size 18×14 is subsequently upsampled using Bilinear interpolation to the original whole image size.

At block 154, ROIs (Regions of Interest) of the mammographic images are selected based on the heatmaps. For example, the selection of the ROIs is achieved by thresholding the heatmap at a fixed value. The threshold used is an empirical value that has been determined after multiple experiments on a large set of mammogram images. The thresholding operation identifies and selects specific ROIs, where the probability is higher than the set threshold. These identified and selected ROIs exhibit the highest contribution towards a particular diagnosis of a mammogram.

At block 156, local features associated with the identified and selected ROIs of the mammographic images are extracted, based on both the heatmaps and the mammographic images. Details of the operations of the block 156 are shown in FIG. 7.

The operations of the block 156 can be implemented by Computer Vision techniques. These local features represent the local characteristics of these ROIs including but not limited to area, shape, intensity and texture features from these ROIs.

Figure 7:
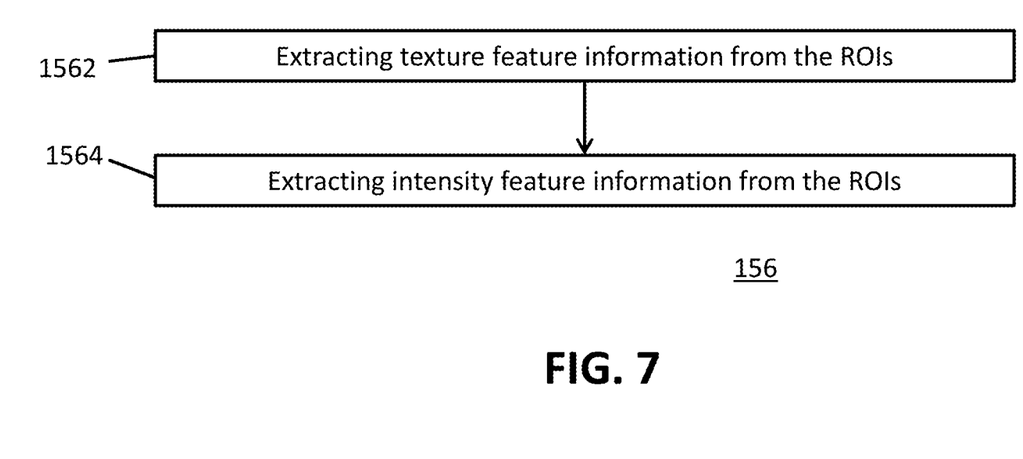
FIG. 7 is a flow diagram illustrating a process of FIG. 5.

As shown in FIG. 7, at block 1562, texture feature information is extracted from the ROIs. For example, the texture feature information can be extracted by using certain texture extraction techniques, which include Run Length Encoding (RLE), Local Binary Patterns (LBP) and Gray Level Co-occurrence Matrix (GLCM). The extracted texture features can assist the users to capture the statistical variations in a given ROI These variations can be statistically correlated to specific objects or features in the mammographic images.

At block 1564, intensity feature information is extracted from the ROIs. For example, the mean, maximum, minimum and median values of intensity in a given ROI are obtained. These local intensity features can assist the users to extract fine-grain information about key pathologies in the mammographic images, which is normally difficult to obtain at a larger scale. Furthermore, certain information that can be effectively extracted at the lower scale includes density and shape of masses, which is highly correlated with a mass being benign or malignant. In addition, image intensity in a particular region also has a high correlation with presence of abnormalities, and masses of abnormalities on average have a higher intensity compared to rest of the breast tissue. Other features having high intensities (such as, presence of isolated bright spots in images) are associated with benign calcifications, while clusters of such bright spots are associated with malignant calcifications. The extracted local features can also be used independently for extracting features from whole mammograms, which can be followed by classification techniques for generating likelihood scores.

At the block 160, the global features and the local features are combined or fused to generate an indicator representative of likelihood of malignancy of target breast tissue. Specifically, the global features extracted through the deep learning algorithm and the local features extracted from the ROIs are combined or fused and further processed. A resultant fused feature vector is generated for both CC and MLO views of the breast, and subsequently concatenated to be used as a single feature for final classification.

For the operation of this block, feature selection techniques can be initially used to reduce the size of the inputted global features and local features. Subsequently, a Recursive Feature Elimination technique can be used to identify the most appropriate predictors, which are the predictors that have the highest contribution towards the final prediction. By removing redundant predictors, calculating time and computational resources can be saved. Furthermore, models trained with redundant predictors have a higher probability of over-fitting, which can result in the system being biased towards the training data. In addition, the final operation is to classify, by using a Random Forest classifier which is trained, the input features as either benign or malignant, based on labels derived from biopsy results. The classifier can be selected based on performance of specific datasets; alternatively, the classifier can be other machine learning algorithms, such as, Neural Networks or SVMs. The output of the classifier is an indicator representative of likelihood of malignancy of target breast tissue.

Figure 8:
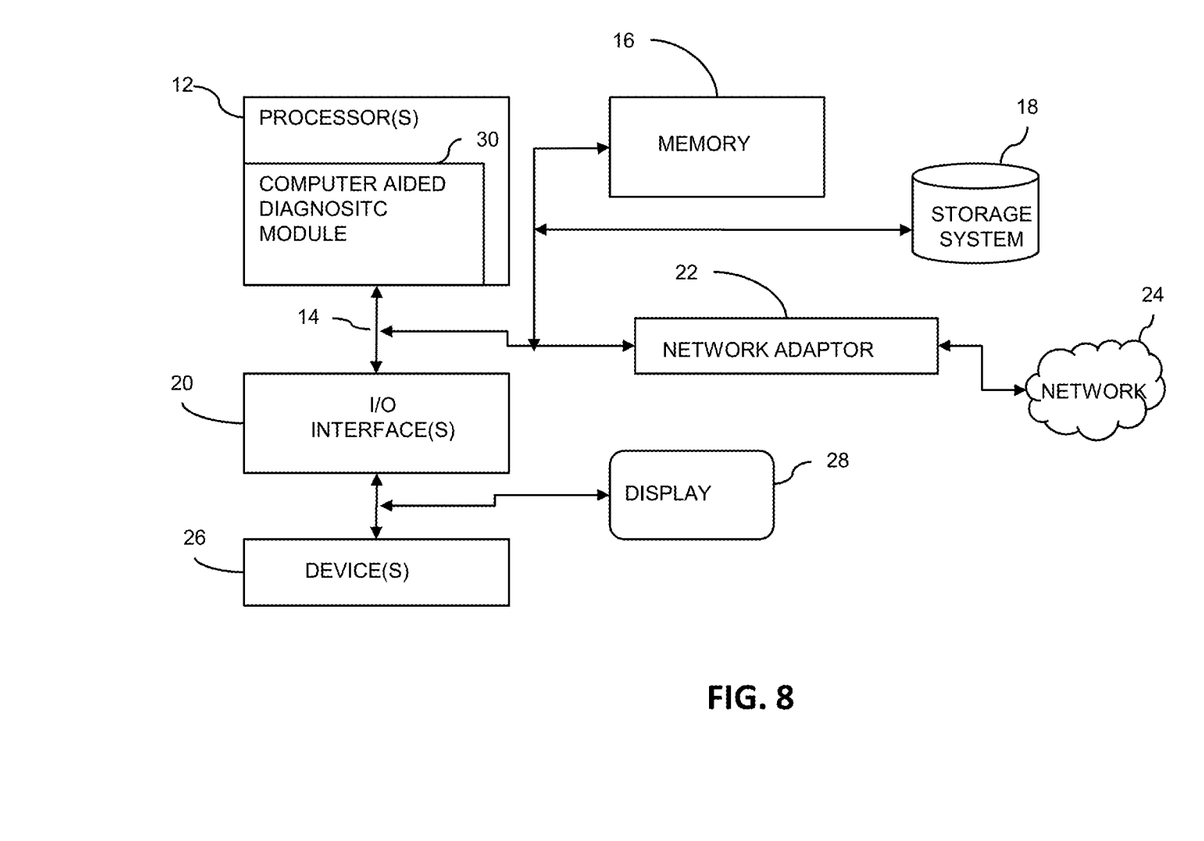
FIG. 8 is a block diagram of an exemplary processing system on which or with which embodiments of the disclosure may be implemented.

FIG. 8 illustrates a schematic of an example computer or processing system that can implement a computer aided diagnostic method for processing mammographic images of target breast tissue.

The computer system is only one example of a suitable processing system and is not intended to suggest any limitation as to the scope of use or functionality of embodiments of the methodology described herein. The processing system shown can be operational with numerous other general purpose or special purpose computing system environments or configurations. Examples of well-known computing systems, environments, and/or configurations that can be suitable for use with the processing system shown in FIG. 8 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, supercomputers, and distributed cloud computing environments that include any of the above systems or devices, and the like.

The computer system can be described in the general context of computer system executable instructions, such as program modules, being executed by a computer system. Generally, program modules may include routines, programs, objects, components, logic, data structures, and so on that perform particular tasks or implement particular abstract data types. The computer system can be practiced in distributed cloud computing environments where tasks are performed by remote processing devices that are linked through a communications network. In a distributed cloud computing environment, program modules can be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 (e.g., a diagnostic module 30) that performs the methods described herein. The module 30 can be programmed into the integrated circuits of the processor 12, or loaded from the system memory 16, storage device 18, or network 24 or combinations thereof.

The bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media can be any available media that is accessible by computer system, and it may include both volatile and non-volatile media, removable and non-removable media.

The system memory 16 can include computer system readable media in the form of volatile memory, such as random access memory (RAM) and/or cache memory or others. Computer system may further include other removable/non-removable, volatile/non-volatile computer system storage media. By way of example only, the storage system 18 can be provided for reading from and writing to a non-removable, non-volatile magnetic media (e.g., a hard drive). Although not shown, a magnetic disk drive for reading from and writing to a removable, non-volatile magnetic disk (e.g., a floppy disk), and an optical disk drive for reading from or writing to a removable, non-volatile optical disk such as a CD-ROM, DVD-ROM or other optical media can be provided. In such instances, each can be connected to the bus 14 by one or more data media interfaces. In some examples, the system memory 16 can include a structure including one or more capacitive processing units as described herein.

Computer system may also communicate with one or more external devices 26, such as, a keyboard, a pointing device, a display 28; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The embodiments of the present invention can be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "or" is an inclusive operator and can mean "and/or", unless the context explicitly or clearly indicates otherwise. It will be further understood that the terms "comprise", "comprises", "comprising", "include", "includes", "including", and/or "having," when used herein, can specify the presence of stated features, integers, steps, operations, elements, and/or components, but do not preclude the presence or addition of one or more other features, integers, steps, operations, elements, components, and/or groups thereof. As used herein, the phrase "in an embodiment" does not necessarily refer to the same embodiment, although it may. As used herein, the phrase "in one embodiment" does not necessarily refer to the same embodiment, although it may. As used herein, the phrase "in another embodiment" does not necessarily refer to a different embodiment, although it may. Further, embodiments and/or components of embodiments can be freely combined with each other unless they are mutually exclusive.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer aided diagnostic method for processing mammographic images of target breast tissue, comprising:
   processing the mammographic images to generate at least one modified image;
   applying a deep learning algorithm comprising a tailored Convolutional Neural Networks (CNN) model to the at least one modified image to generate a first output and a second output;
   extracting global features associated with the entirety of the mammographic images by using the first output;
   extracting local features associated with Regions of Interest (ROIs) of the mammographic images by using the second output; and
   combining the global features and the local features to generate an indicator representative of likelihood of malignancy of the target breast tissue;
   wherein the processing the mammographic images to generate at least one modified image comprises:
   applying a median filter to the mammographic images to eliminate noises and artifacts of the mammographic images;
   applying an adaptive histogram equalization to the mammographic images to enhance contrast of the mammographic images; and generating the at least one modified image based on the enhanced mammographic images with the noises and artifacts eliminated.

2. The method according to claim 1, wherein the applying a deep learning algorithm comprising a tailored Convolutional Neural Networks (CNN) model to the at least one modified image to generate a first output and a second output comprises:
   obtaining an output at the Global Average Pooling (GAP) layer of the tailored CNN model as the first output used for extracting global features associated with the entirety of the mammographic images; and
   obtaining an output at the final Activation layer of the tailored CNN model as the second output used for extracting local features associated with ROIs of the mammographic images.

3. The method according to claim 1, wherein the extracting local features associated with Regions of Interest (ROIs) of the mammographic images by using the second output comprises:
   generating at least one heatmap based on the second output;
   selecting the ROIs based on the at least one heatmap; and
   extracting the local features associated with the selected ROIs based on the at least one heatmap and the mammographic images.

4. The method according to claim 3, wherein the extracting the local features associated with the selected ROIs comprises:
   extracting texture feature information from the ROIs; and
   extracting intensity feature information from the ROIs.

5. A system for processing mammographic images of target breast tissue, comprising:
   a hardware processor; and
   a memory coupled with the hardware processor,
   wherein the hardware processor is configured to at least:
      process the mammographic images to generate at least one modified image;
      apply a deep learning algorithm comprising a tailored Convolutional Neural Networks (CNN) model to the at least one modified image to generate a first output and a second output;
      extract global features associated with the entirety of the mammographic images by using the first output;
      extract local features associated with Regions of Interest (ROIs) of the mammographic images by using the second output; and
      combine the global features and the local features to generate an indicator representative of likelihood of malignancy of the target breast tissue;
   wherein the hardware processor is further configured to:
   apply a median filter to the mammographic images to eliminate noises and artifacts of the mammographic images;
   apply an adaptive histogram equalization to the mammographic images to enhance contrast of the mammographic images; and
   generate the at least one modified image based on the enhanced mammographic images with the noises and artifacts eliminated.

6. The system according to claim 5, wherein the hardware processor is further configured to:
   obtain an output at the Global Average Pooling (GAP) layer of the tailored CNN model as the first output used for extracting global features associated with the entirety of the mammographic images; and
   obtain an output at the final Activation layer of the tailored CNN model as the second output used for extracting local features associated with ROIs of the mammographic images.

7. The system according to claim 5, wherein the hardware processor is further configured to:
   select the ROIs based on the at least one heatmap; and
   extract the local features associated with the selected ROIs based on the at least one heatmap and the mammographic images.

8. The system according to claim 7, wherein the hardware processor is further configured to:
   extract texture feature information from the ROIs; and
   extract intensity feature information from the ROIs.

9. A computer program product for processing mammographic images of target breast tissue, the computer program product comprising a computer readable non-transitory storage medium having program instructions embodied therewith, the program instructions executable by a processing element of a device to cause the device to:
   process the mammographic images to generate at least one modified image;
   apply a deep learning algorithm comprising a tailored Convolutional Neural Networks (CNN) model to the at least one modified image to generate a first output and a second output;
   extract global features associated with the entirety of the mammographic images by using the first output;
   extract local features associated with Regions of Interest (ROIs) of the mammographic images by using the second output; and
   combine the global features and the local features to generate an indicator representative of likelihood of malignancy of the target breast tissue;
   wherein the program instructions are further executable by the processing element of the device to cause the device to:
   apply a median filter to the mammographic images to eliminate noises and artifacts of the mammographic images;
   apply an adaptive histogram equalization to the mammographic images to enhance contrast of the mammographic images; and
   generate the at least one modified image based on the enhanced mammographic images with the noises and artifacts eliminated.

10. The computer program product according to claim 9, wherein the program instructions are further executable by the processing element of the device to cause the device to:
   obtain an output at the Global Average Pooling (GAP) layer of the tailored CNN model as the first output used for extracting global features associated with the entirety of the mammographic images; and
   obtain an output at the final Activation layer of the tailored CNN model as the second output used for extracting local features associated with ROIs of the mammographic images.

11. The computer program product according to claim 9, wherein the program instructions are further executable by the processing element of the device to cause the device to:
   select the ROIs based on the at least one heatmap; and
   extract the local features associated with the selected ROIs based on the at least one heatmap and the mammographic images.

12. The computer program product according to claim 11, wherein the program instructions are further executable by the processing element of the device to cause the device to:

extract texture feature information from the ROIs; and
extract intensity feature information from the ROIs.

13. A computer aided diagnostic method for processing mammographic images of target breast tissue, comprising:
processing the mammographic images to generate at least one modified image;
applying a deep learning algorithm comprising a tailored Convolutional Neural Networks (CNN) model to the at least one modified image to generate a first output and a second output;
extracting global features associated with the entirety of the mammographic images by using the first output;
extracting local features associated with Regions of Interest (ROIs) of the mammographic images by using the second output; and
combining the global features and the local features to generate an indicator representative of likelihood of malignancy of the target breast tissue;
wherein the applying a deep learning algorithm comprising a tailored Convolutional Neural Networks (CNN) model to the at least one modified image to generate a first output and a second output comprises:
obtaining an output at the Global Average Pooling (GAP) layer of the tailored CNN model as the first output used for extracting global features associated with the entirety of the mammographic images; and
obtaining an output at the final Activation layer of the tailored CNN model as the second output used for extracting local features associated with ROIs of the mammographic images.

14. A computer aided diagnostic method for processing mammographic images of target breast tissue, comprising:
processing the mammographic images to generate at least one modified image;
applying a deep learning algorithm comprising a tailored Convolutional Neural Networks (CNN) model to the at least one modified image to generate a first output and a second output;
extracting global features associated with the entirety of the mammographic images by using the first output;
extracting local features associated with Regions of Interest (ROIs) of the mammographic images by using the second output; and
combining the global features and the local features to generate an indicator representative of likelihood of malignancy of the target breast tissue;
wherein the extracting local features associated with Regions of Interest (ROIs) of the mammographic images by using the second output comprises:
generating at least one heatmap based on the second output;
selecting the ROIs based on the at least one heatmap; and
extracting the local features associated with the selected ROIs based on the at least one heatmap and the mammographic images.

15. The method of claim 14 wherein the extracting the local features associated with the selected ROIs comprises:
extracting texture feature information from the ROIs; and
extracting intensity feature information from the ROIs.

* * * * *